United States Patent [19]

Liu et al.

[11] Patent Number: 5,834,210
[45] Date of Patent: Nov. 10, 1998

[54] STABLE TROPONIN SUBUNITS AND COMPLEXES

[75] Inventors: Shigui Liu, Toronto; Qinwei Shi, Etobicoke, both of Canada

[73] Assignee: Spectral Diagnostics, Inc., Toronto, Canada

[21] Appl. No.: 961,858

[22] Filed: Oct. 31, 1997

Related U.S. Application Data

[63] Continuation-in-part of Ser. No. 862,613, May 23, 1997, abandoned.

[51] Int. Cl.⁶ .................................................... G07K 14/47
[52] U.S. Cl. .......................... 435/7.1; 530/402; 530/403; 530/530; 435/69.1
[58] Field of Search ..................................... 435/69.1, 7.1; 530/350, 402, 403

[56] References Cited

U.S. PATENT DOCUMENTS

| | | | |
|---|---|---|---|
| 4,946,778 | 8/1990 | Ladner et al. | 435/69.1 |
| 5,290,678 | 3/1994 | Jackowski | 435/7.4 |
| 5,560,937 | 10/1996 | Lee et al. | 424/569 |
| 5,583,200 | 12/1996 | Larue et al. | 530/350 |
| 5,604,105 | 2/1997 | Jackowski | 435/7.4 |

FOREIGN PATENT DOCUMENTS

| | | |
|---|---|---|
| 0743522 | 11/1996 | European Pat. Off. . |
| WO 97/19955 | 6/1997 | WIPO . |

OTHER PUBLICATIONS

Farah et al. "The troponin complex and regulation of muscle contraction" FASEB Journal (USA), 1995, 9/9 (755–767), Jun. 1, 1995.
Armour et al.(1993), Gene, 131:287–292.
Cummins et al.,(1978), Biochem. J., 171:251–259.
Fujita–Becker et al.(1993), J. Biochem., 114:438–444.
Al–Hillawi et al.(1994), Eur. J. Biochem., 225:1195–1201.
Hu et al.(1996), Protein Expression and Purification, 7:289–293.
Mair et al.(1995), Clin. Chem. 41:1266–1272.
Malnic et al.(1994), Eur. J. Biochem., 222:49–54.
Newby et al.(1995), Clin. Chem., 41:1263–1265.
Syska et al.(1974), FEBS letts., 40:253–257.
Tsukui et al.(1973), J. Biochem., 73:1119–1121.
Vallins et al.(1990), FEBS Letts., 270:57–61.

*Primary Examiner*—Robert A. Wax
*Assistant Examiner*—Bradley S. Mayhew
*Attorney, Agent, or Firm*—Klauber & Jackson

[57] ABSTRACT

Stable troponin subunits and complexes and methods for their preparation are described. Among other uses, these subunits and complexes are useful as antigens for the preparation of antibodies, and as controls and calibrators for troponin assays. One complex comprises a modified human cardiac troponin I together with human cardiac troponin T and human cardiac troponin C. Another complex comprises a modified human cardiac troponin I with human cardiac troponin C.

10 Claims, 5 Drawing Sheets

FIG. 1A

```
                    G   T   G AG
  1 ATG GCT AGC ATG GGA TCT ATG GCA GAC GGT TCC AGC GAT GCG GCT    45
  1  M   A   S   M   G   S   M   A   D   G   S   S   D   A   A    15

46 AGG GAA CCT CGC CCT GCA CCA GCC ATC AGA CGC TCC TCC            90
 16  R   E   P   R   P   A   P   A   I   R   R   S   S            30

91 AAC TAC CGC GCT TAT GCC ACG GAG CCG CAC GCC AAG AAA AAA TCT   135
 31  N   Y   R   A   Y   A   T   E   P   H   A   K   K   K   S    45

136 AAG ATC TCC GCC TCG AGA AAA TTG CAG CTG AAG ACT CTG CTG CTG   180
 46  K   I   S   A   S   R   K   L   Q   L   K   T   L   L   L    60

181 CAG ATT GCA AAG CAA GAG CTG GAG CGA GAG GCG GAG GAG CGG CGC   225
 61  Q   I   A   K   Q   E   L   E   R   E   A   E   E   R   R    75

226 GGA GAG AAG GGG CGC GCT CTG AGC ACC CGC TGC CAG CCG CTG GAG   270
 76  G   E   K   G   R   A   L   S   T   R   C   Q   P   L   E    90

271 TTG GCC GGG CTG GGC TTC GCG GAG CTG CAG GAC TTG TGC CGA CAG   315
 91  L   A   G   L   G   F   A   E   L   Q   D   L   C   R   Q   105

316 CTC CAC GCC CGT GTG GAT GAC AAG GTG GAT GAA GAG TAC GAC ATA   360
106  L   H   A   R   V   D   D   K   V   D   E   E   Y   D   I   120
```

FIG. 1B

```
361 GAG GCA AAA GTC ACC AAG AAC ATC ACG GAG ATT GCA GAT CTG ACT  405
121  E   A   K   V   T   K   N   I   T   E   I   A   D   L   T  135
406 CAG AAG ATC TTT GAC CTT CGA GGC AAG TTT AAG CGG CCC ACC CTG  450
136  Q   K   I   F   D   L   R   G   K   F   K   R   P   T   L  150
451 CGG AGA GTG AGG ATC TCT GCA GAT GCC ATG ATG CAG GCG CTG CTG  495
151  R   R   V   R   I   S   A   D   A   M   M   Q   A   L   L  165
496 GGG GCC CGG GCT AAG GAG TCC CTG GAC CTG CGG GCC CAC CTC AAG  540
166  G   A   R   A   K   E   S   L   D   L   R   A   H   L   K  180
541 CAG GTG AAG AAG GAG GAC ACC GAG AAG AAC CGG GAG GTG GGA      585
181  Q   V   K   K   E   D   T   E   K   N   R   E   V   G      195
586 GAC TGG CGC AAG AAC ATC GAT GCA CTG AGT GGA ATG GAG GGC CGC  630
196  D   W   R   K   N   I   D   A   L   S   G   M   E   G   R  210
631 AAG AAA AAG TTT GAG AGC TGA                                  651
211  K   K   K   F   E   S   *                                  217
```

FIG.2A

```
  1 ATG TCT GAC ATA GAA GAG GTG GAA GAG TAC GAG GAG GAG GAG       45
  1 Met Ser Asp Ile Glu Glu Val Val Glu Glu Tyr Glu Glu Glu       15

46 CAG GAA GAA GCA GCT GTT GAA GAG CAG GAG CAG GAA GCG GAG       90
 16 Gln Glu Glu Ala Ala Val Glu Glu Gln Glu Gln Glu Ala Glu       30

91 GAT GCT GAA GCA GAG GCT GAG GCA GAG ACC GAG GAG GCA GAA      135
 31 Asp Ala Glu Ala Glu Ala Glu Ala Glu Thr Glu Glu Ala Glu       45

136 GAT GAA GAA GAA GAA GCA AAG GAG GCT GAA GAT GGC CCA ATG      180
 46 Asp Glu Glu Glu Glu Ala Lys Glu Ala Glu Asp Gly Pro Met       60

181 GAG GAG TCC AAA CCC AAG CCC AGG TCG TTC ATG CCC AAC TTG GTG  225
 61 Glu Glu Ser Lys Pro Lys Pro Arg Ser Phe Met Pro Asn Leu Val   75

226 CCT CCC AAG ATC CCC GAT GGA GAG AGA GTG GAC TTT GAT GAC ATC  270
 76 Pro Pro Lys Ile Pro Asp Gly Glu Arg Val Asp Phe Asp Asp Ile   90

271 CAC CGG AAG CGC ATG GAG AAG GAC CTG AAT GAG TTG CAG GCG CTG  315
 91 His Arg Lys Arg Met Glu Lys Asp Leu Asn Glu Leu Gln Ala Leu  105

316 ATT GAG GCT CAC TTT GAG AAC AGG AAA AAG GAG GAG GAG CTC      360
106 Ile Glu Ala His Phe Glu Asn Arg Lys Lys Glu Glu Glu Leu      120

361 GTT TCT CTC AAA GAC AGG ATC GAG CGT CGG GCA GAG CGG GCC      405
121 Val Ser Leu Lys Asp Arg Ile Glu Arg Arg Ala Glu Arg Ala      135
```

FIG. 2B

```
361 GTT TCT CTC AAA GAC AGG ATC GAG AGA CGT CGG GCA GAG CGG GCC     405
121 Val Ser Leu Lys Asp Arg Ile Glu Arg Arg Arg Ala Glu Arg Ala    135

406 GAG CAG CAG CGC ATC CGG AAT GAG CGG GAG AAG GAG CGG CAG AAC     450
136 Glu Gln Gln Arg Ile Arg Asn Glu Arg Glu Lys Glu Arg Gln Asn    150

451 CGC CTG GCT GAA GAG AGG GCT CGA CGA CGA GAG GAG GAG AAC AGG     495
151 Arg Leu Ala Glu Glu Arg Ala Arg Arg Arg Glu Glu Glu Asn Arg    165
            AGG

496 CGT AAG GCT GAT GAG GCC CGG AAG AAG GCT TTG TCC AAC             540
166 Arg Lys Ala Asp Glu Ala Arg Lys Lys Ala Leu Ser Asn            180

541 ATG ATG CAT TTT GGG GGT TAC ATC CAG ACT GAG CGG CAG ACA GAG     585
181 Met Met His Phe Gly Gly Tyr Ile Gln Thr Glu Arg Gln Thr Glu    195

586 CGG AAA AGT GGG AAG AGG CAG ACT GAG CGG GAA AAG AAG AAG AAG     630
196 Arg Lys Ser Gly Lys Arg Gln Thr Glu Arg Glu Lys Lys Lys Lys    210
                    AGG
                    AGG

631 ATT CTG GCT GAG CGT AAG GTG CTG GCC ATT GAC CAC CTG AAT         675
211 Ile Leu Ala Glu Arg Lys Val Leu Ala Ile Asp His Leu Asn        225

676 GAA GAT CAG CTG AGG CGT AAG GAG GCC AAG GAG CTG TGG CAG AGC ATC 720
226 Glu Asp Gln Leu Arg Arg Lys Glu Ala Lys Glu Leu Trp Gln Ser Ile 240
```

FIG.2C

```
721 TAT AAC TTG GAG GCA GAG AAG TTC GAC CTG CAG GAG AAG TTC AAG  765
241 Tyr Asn Leu Glu Ala Glu Lys Phe Asp Leu Gln Glu Lys Phe Lys  255

766 CAG CAG AAA TAT GAG ATC AAT GTT CTC CGA AAC AGG ATC AAC GAT  810
256 Gln Gln Lys Tyr Glu Ile Asn Val Leu Arg Asn Arg Ile Asn Asp  270

811 AAC CAG AAA GTC TCC AAG ACC CGC GGG AAG GCT AAA GTC ACC GGG  855
271 Asn Gln Lys Val Ser Lys Thr Arg Gly Lys Ala Lys Val Thr Gly  285

856 CGC TGG AAA TAG                                              867
286 Arg Trp Lys ***                                              289
```

STABLE TROPONIN SUBUNITS AND COMPLEXES

CROSS-REFERENCE TO RELATED APPLICATION

This application is a continuation-in-part of copending and commonly owned application Ser. No. 08/862,613, filed May 23, 1997, now abandoned.

FIELD OF THE INVENTION

This invention relates to recombinantly-expressed human cardiac troponin subunits I, C, and T, recombinant human cardiac troponin complexes made in vitro therefrom, and methods for the production and purification of the subunits and the preparation of the complexes.

BACKGROUND OF THE INVENTION

Early and accurate assessment of suspected acute myocardial infarction is critically dependent on the sensitive and specific detection and quantitation in blood, serum or plasma of released cardiac muscle intracellular components in order to distinguish a potentially lethal event in need of emergency measures from non-life threatening conditions such as angina and non-cardiac chest pain such as dyspepsia. Early electrocardiographic changes are not adequately specific, and the medical profession has come to rely on serum biochemical markers of cardiac tissue necrosis for early diagnosis. Initially, the serum markers creatine kinase (CK) and specifically the cardiac CK-MB isoform were used, and subsequently myoglobin as a more sensitive early indicator of cardiac damage. More recently, the highly sensitive markers cardiac troponin subunits I and T have come to be preferred for their extraordinarily high specificity for identifying myocardial damage. These tests, along with other markers of skeletal muscle necrosis, provide a high degree of diagnostic accuracy. If performed in the emergency room, an early and accurate diagnosis of myocardial damage offers great advantage to a suspected heart attack victim.

Diagnostic tests employing highly sensitive cardiac markers are described, for example, in U.S. Pat. Nos. 5,604,105 and 5,290,678. These procedures offer the rapidity of diagnosing myocardial infarction in the emergency room setting and offer significant medical benefit for patients.

Though numerous diagnostic assays for troponin subunits, principally I and T, exist, for example the troponin I Stratus(R) test from Dade International, Inc., the Opus(R) test from Behring, and the Access(R) test from Sanofi, there is no troponin subunit or complex preparation of sufficient quality and stability to employ as a standard for calibration of assays nor to use as a universally acceptable consensus standard across the industry. In order to maintain the conformational structure of troponin I, it must be complexed with troponin C. Troponin preparations from one source and for one particular assay format may not be useable in another, thus it is not currently possible to use the same standard across tests from different manufacturers. The lack of a industry-accepted standard limits the establishment of industry guidelines for test criteria as well as comparison of results throughout the world to help establish normal and abnormal value ranges.

Numerous troponin preparations from both natural and recombinant sources have been proposed. Previously described methods for the purification of troponin subunits from cardiac tissue (Tsukui et al., 1973, J. Biochem., v. 73, pp. 1119–1121; Cummins et al., 1978, Biochem. J., v. 171, pp. 251–259; Syska et al., 1974, FEBS Letts., v. 40, pp. 253–257) yielded preparations which were unstable and subject to considerable degradation on storage. A troponin complex prepared from cardiac tissue or from the combination of isolated troponin subunits prepared from cardiac tissue has been described (EP 0 743 522 A1). DE4405249 (U.S. Pat. No. 5,583,200) describes a stabilized troponin I or T also containing troponin C, with stability of several days in the cold. Use of a combination of four protease inhibitors in U.S. Pat. No. 5,560,937 overcame the degradation and stability issues inherent in tissue-derived troponin I, but did not obviate the need for human heart tissue. Unfortunately, human tissue is a potential source of infection, including HIV and hepatitis, to workers during troponin purification, and human heart tissue is of increasing scarcity especially with the successful use of early diagnostic tests for heart attack responsible for decreasing mortality from this disease. Troponin standards prepared by recombinant means offer a less costly and less hazardous alternative to that from heart tissue, but may still suffer from a lack of stability incompatible with industry demands.

Recombinant troponin subunits and complexes have been described. Armour et al. (1993, Gene, v. 131, pp. 287–292) cloned human cardiac troponin I in a bacterial system and expressed the gene product both as a beta-gal fusion product, and as an unfused product. Al-Hillawi et al. (1994, Eur. J. Biochem., v. 225, pp. 1195–1201) expressed human cardiac troponin I and troponin C in *E. coli*, using two codon changes in the cDNA of the former to overcome difficulties in expressing the human product in bacteria. Malnic and Reinach (1994, Eur. J. Biochem., v. 222, pp. 49–54) produced a recombinant complex in vivo by cloning all three chicken skeletal muscle troponin subunits into an expression plasmid. The troponin complex formed within the bacterium. Fujita-Becker et al. (1993, J. Biochem., v. 114, pp. 438–444) described the reconstitution of rabbit skeletal troponin complex from recombinant subunits expressed in *E. coli*. None of these recombinant products has been demonstrated to have adequate stability for use as a diagnostic test standard or calibrator. A recombinant human cardiac troponin complex formed in vitro from recombinant human cardiac troponin I, recombinant human cardiac troponin T, and recombinant human cardiac troponin C has not been described previously, nor has a complex formed of recombinant human cardiac troponin I and recombinant human cardiac troponin C.

Thus, there is a need for troponin complexes which meet the requirements of a stable material of safe origin and economical preparation that may be used as controls or calibrators across troponin assays. It has now been discovered that human cardiac troponin complexes prepared from recombinant subunits offer, among other advantages, superior stability and utility among troponin assays to be suitable for use as a universal standard.

SUMMARY OF THE INVENTION

The present invention relates to a recombinant human cardiac troponin complex comprising a recombinant modified human cardiac troponin I, recombinant human cardiac troponin C, and recombinant human cardiac troponin T, the complex formed in vitro from the individual recombinant troponin subunits. The invention also comprises a complex formed of recombinant modified human cardiac troponin I and recombinant human cardiac troponin C. The present invention also relates to a novel recombinant human cardiac troponin I subunit with a modified cDNA and protein sequence with improved expression in *E. coli*. The troponin complexes prepared in vitro from the recombinantly expressed subunits are of higher stability than previously reported troponin complexes prepared from recombinant methods or from troponin subunits isolated from cardiac tissue. They can be used as controls or calibrators among different troponin assay procedures. In contrast, previously known troponins cannot be so employed.

The subunits and complexes are also useful as antigens to prepare antibodies useful for a variety of purposes.

The troponin subunits are prepared by recombinant techniques, expressed and optionally purified individually before admixture to prepare the complexes. The complex may be purified by standard procedures after they are formed. Recombinant expression of the troponin subunits can be optimized. Troponin I is engineered as a recombinant product with an additional N-terminal portion of from about 4 to about 12, preferably 5 to 8, amino acids. It has been observed that the additional amino acids increase the expression of modified troponin I in *E. coli*. Troponin T has been expressed at high levels by altering arginine codons in the cDNA to be compatible with the bacterial expression system, without altering the amino acid sequence of the subunit. Recombinant troponin C is expressed with the native amino acid sequence.

Modified Troponin I as used herein refers to Troponin I with additional N-terminal acids to increase the expression of the desired product. It is not essential that the amino acids be identical with or in the same order as shown in the figure.

The subunits are prepared separately before being brought together in vitro under selected conditions to form the troponin complexes. Conditions are selected to promote complex formation, including the use of an alkaline earth salt or salts and, if desired, a detergent for the complex of troponins C, I and T. One or more alkaline earth salts, and a chaotropic agent, may be employed in the preparation of the complex of troponin C and I. Calcium chloride and magnesium chloride are preferred as alkaline earth salts. As the detergent, sodium dodecyl sulfate is preferred. Urea is the preferred chaotropic agent.

It is an objective of the present invention to provide a recombinant human cardiac troponin I protein of SEQ ID NO:5 which has an additional N-terminus of about 6 amino acids and other codon changes which facilitates the recombinant expression of the protein. It is a further objective of this invention to provide a recombinant human cardiac troponin T protein produced from a cDNA sequence set forth in SEQ ID NO:4 which has certain codon changes in the cDNA but no change in protein sequence compared to native human cardiac troponin T.

According to the present invention, a method is provided for the preparation of human cardiac troponin complexes prepared from recombinant modified troponin I, recombinant troponin C, and recombinant troponin T. The method comprises the steps of: 1) expressing the troponin subunits recombinantly; 2) optionally purifying the separate subunits; 3) admixing the subunits preferably in the presence of at least one alkaline earth salt or salts and, if desired, a detergent, to form the troponin complex. The use of a detergent increases the yield and purity of the products. It is a further object of the invention to provide a method for the preparation of a human cardiac troponin complex prepared from recombinant modified troponin I and recombinant troponin C, comprising the steps of: 1) expressing the troponin subunits recombinantly; 2) admixing the subunits preferably in the presence of an alkaline earth salt or salts and a chaotropic agent to form the troponin complex. Purification is preferably effected before formation of a complex. The present invention contemplates modifications to the DNA sequence of the troponin subunits to facilitate their expression in their respective recombinant systems.

The recombinant troponin complexes according to the present invention have the purity and stability characteristics to enable utility as assay controls and calibrators for use in the diagnostics industry for the manufacture, quality control, and calibration of troponin assays. The troponin complexes of the present invention show superior stability compared to existing troponin complexes, and may be utilized as controls among different troponin assay procedures, in contrast to existing troponin controls which cannot be used except in the specific assays for which they were designed.

It is a further advantage of the present invention that production of the recombinant human cardiac troponin complexes is independent of the availability of human cardiac tissue. Working with human tissues presents an inherent risk of infection by any number of diseases including HIV and hepatitis. In addition, the quality of tissue may be unknown resulting in the production of an inferior product. Heart tissue from elderly individuals may be hypertrophic and as a result have a low muscle mass and thus not provide a satisfactory quantity or quality of troponin. Human heart tissue is prohibitively costly as a long-term, consistent source of troponin to meet the future demands of the rapidly expanding field of emergency cardiac diagnostics.

Another advantage of the present invention is the ease of purification compared to products isolated from human cardiac tissue. Consequently, the authenticity and purity of each subunit can be simply determined prior to the preparation of the complexes. The lack of uniformity of tissue, presence of degradation or autolysis products, etc., are obviated by use of the individual recombinant subunits rather than products isolated from natural sources.

A further advantage of the present invention is that it provides a novel recombinant modified human cardiac troponin I that may be used as an assay control or calibrator.

A still further advantage is that the invention provides recombinant troponin subunits of sufficient purity and quantity to permit their use as controls or calibrators and also to serve as substrates from which to produce stable troponin complexes that meet the purity and stability requirements to be used as an assay standard or calibrator.

These and other advantages of the recombinant human cardiac troponin complexes and its subunits in the present invention will be apparent upon consideration of the following detailed description.

BRIEF DESCRIPTION OF THE DRAWINGS

FIG. 1 represents the DNA (SEQ ID NO: 1) and protein (SEQ ID NO: 5) sequences of the recombinant modified human cardiac troponin I of the present invention. The box points out the six amino acid residues added to the N-terminus of human cardiac troponin I. The original bases (SEQ ID NO: 3, including the additional N-terminal amino acids) are shown above the altered sequences.

FIG. 2 represents the DNA (SEQ ID NO: 4) and protein (SEQ ID NO: 6) sequences of the recombinant human cardiac troponin T of the present invention. The codons which replace the natural codon is underlined, and the natural codon is shown above. The native troponin T DNA sequence is shown in SEQ ID NO: 2.

DETAILED DESCRIPTION OF THE INVENTION

Measurement in circulation of the cardiac muscle-associated protein troponin and, particularly, its components I and T, has proven to be an early and specific indicator of suspected acute myocardial infarction. As such, numerous methods for rapidly and accurately detecting troponin and its subunits in blood have been and are being developed for diagnosing heart attack in an emergency situation, and countless lives have been and will be saved as a result. However, in order to develop accurate and dependable diagnostic assays and to calibrate them, the availability of stable, high-quality human cardiac troponin controls is critical for quality control and testing purposes. This invention provides pure, stable, recombinant human cardiac troponin complexes to meet the needs of the industry. A troponin complex may be formed in vitro from the admixture of recombinantly expressed human cardiac troponin I, troponin T and troponin C. Another troponin complex may be formed from the admixture of recombinantly expressed human cardiac troponin I and C.

Troponin I may be engineered as a recombinant product with about 6 additional amino acid N-terminal residues (see FIG. 1; SEQ ID NO:5) to increase its expression in E. coli. In addition, certain codon changes have been made in the cDNA sequence to optimize expression of the protein in E. coli, without change in the amino acid sequence. The modified recombinant troponin I may be isolated from the bacterial host and purified by standard protein purification methods following details illustrated in the examples below. The purified modified troponin I is then be employed as an antigen or to prepare the recombinant troponin complexes such as that of troponin I, troponin C and troponin T, and that of troponin I and troponin C. Troponin C stabilizes the conformational structure of troponin I. In addition, the recombinant, modified human cardiac troponin I has utility itself as an improved control or calibrator.

Recombinant troponin T has been expressed at high levels by altering arginine codons in the cDNA (see FIG. 2; SEQ ID NO:4) to be compatible with the bacterial expression system, without altering the amino acid sequence of the subunits. The recombinant troponin T is isolated from the bacterial host and, optionally, purified by standard protein purification methods following details in the example below. The recombinant troponin T produced by this method has utility itself as an improved control or calibrator.

The troponin C is expressed in E. coli in its native amino acid sequence, then isolated from the bacterial host and optionally purified by standard protein purification methods following details illustrated in the examples below.

Typically, the subunits are prepared separately and optimally purified before being brought together in vitro under selected conditions to form the complex of troponin I, T and C. Conditions are selected to promote complex formation, including the use of an alkaline earth salt or salts and, if desired, a detergent. As the alkaline earth salts, calcium chloride and magnesium chloride are preferred. As the detergent, sodium dodecyl sulfate is preferred. For the complex of troponin I and C, conditions are selected to promote complex formation including the use of an alkaline earth salt or salts and a chaotropic agent. As the alkaline earth salts, calcium chloride and magnesium chloride are preferred. As the chaotropic agent, urea is preferred.

As will be evident from the examples presented below, the recombinant troponin complexes according to the present invention have purity and stability characteristics to enable their utility as assay controls and calibrators for use in the diagnostics industry for the manufacture, quality control, and calibration of troponin assays. The troponin complexes of the present invention shows superior stability compared to known troponin complexes, and are shown to be detected utilizing different troponin assay methods and instruments, in contrast to existing troponin controls which cannot be used as a standard outside of the specific assay for which they were designed.

The preparation of the recombinant troponin subunits, their purification, and preparation of the complexes are illustrated in the following non-limiting examples, which also demonstrate their stability and utility in various assays.

EXAMPLE 1

Expression and purification of modified human cardiac troponin I

Human cardiac troponin I cDNA was cloned by the polymerase chain reaction (PCR) using primers designed from published cardiac troponin I cDNA sequence (Vallins et al., 1990, FEBS Letters, vol. 270, pp. 57–61, the full disclosure of which is incorporated herein by reference). Since the expression of human cardiac troponin I was very low in E. coli if the original cDNA sequence was used (Armour et al., 1993, Gene, vol. 131, pp. 287–292), both N-terminus addition and codon alteration were performed to increase the yield. The altered human cardiac troponin I cDNA sequence (FIG. 1; SEQ ID NO: 1) was confirmed by DNA sequencing and cloned into plasmid pET21 (Novagen). E. coli BL21 (DE3) cells (Novagen) were transformed with the resulting construct and the protein produced from this expression vehicle analyzed using SDS-PAGE. This E. coli strain has been deposited and has ATCC number.

For purification, the following reagents were used: lysis buffer (50 mM Tris-HCl, 1 mM EDTA, 20 mM 2-mercaptoethanol, 100 mM sodium chloride, pH 8.0); 2M urea-lysis buffer (2M urea in lysis buffer; 8M urea-lysis buffer (8M urea in lysis buffer); dialysis buffer (20 mM Tris-HCl, 100 mM sodium chloride, 10 mM 2-mercaptoethanol, pH 7.5); eluting buffer (20 mM Tris-HCl, 800 mM sodium chloride, 10 mM 2-mercaptoethanol, pH 7.5); final buffer (20 mM Tris-HCl, 500 mM sodium chloride, 60 mM 2-mercaptoethanol, pH 7.5).

The following sequential steps were carried out for the purification of the modified human recombinant troponin I protein. Recombinant bacterial cells were collected by centrifugation of the culture medium. Cells were resuspended in lysis buffer at the ratio of 50 ml lysis buffer per liter equivalent of original culture medium. Lysozyme (10 mg/ml) was added at 1 ml lysozyme per liter of culture medium. The resulting mixture was then shaken at room temperature for 30 minutes. Triton X-100 (10%) was added at 5 ml per liter of culture medium, followed by PMSF (0.1M) at 0.5 ml per liter of medium. The suspension was incubated at 37° C. for 15 minutes. The vessel containing the suspension was submerged in dry ice/ethanol to rapidly freeze the cell suspension. The frozen suspension was then thawed in a 37° C. water bath. The thawed cell suspension was sonicated using a Vibra Cell™ sonicator at 2° C.–8° C. to shear the DNA. The suspension was centrifuged at 20,000 g for 20 min at 2° C.–8° C. and the supernatant was discarded. Fifty ml of 2M urea-lysis buffer and 10 ml of 10% Triton X-100 was added per liter equivalent of original culture medium; the pellet was homogenized and stirred at 4° C. for 15 min. The mixture was then centrifuged at 20,000 g for 20 min at 2° C.–8° C. and the supernatant discarded. 8M urea-lysis buffer (50 ml of urea-lysis buffer per liter cell culture) was added, and the mixture homogenized then stirred for 30 min at room temperature. After centrifugation at 20,000 g at 2° C.–8° C. for 20 min. the pellet is discarded. The supernatant is dialyzed in dialysis buffer overnight, and if required, the dialysate was centrifuged to remove any particulate matter.

The sample was loaded onto a previously equilibrated CM-Sephadex column (for example, a 2.5×20 cm; 100 ml bed volume for 2 L of original culture medium). The column was washed with 4 bed volumes of the dialysis buffer, and eluted with a linear gradient of 3.5 bed volumes of 0–800 mM NaCl (100% dialysis buffer changed over to 100% eluting buffer). The fractions were checked by 15% SDS-PAGE and those containing the troponin I were pooled then dialyzed against final buffer. The dialysate was centrifuged at 20,000 g for 20 min and the supernatant filtered through two layers of Miracloth. In order to remove endotoxin from the protein preparation and form a product useful as an antigen, following Triton X-114 phase separation procedures are performed. Triton X-114 (100%) was added at 1 ml per 100 ml of the supernatant and stirred at 4° C. for 30 min. The sample was incubated at 37° C. for 10 min., then centrifuged at 20,000 g for 5 min at 30° C. using 40-ml centrifuge tubes. After removing the upper aqueous phase with care so as not to aspirate the detergent phase, the aqueous phases were combined. The addition and centrifugation steps with Triton X-114 were repeated two more times. The aqueous phase was dialyzed overnight against the final buffer (100 ml sample per liter of the final buffer).

Final determination of protein concentration was performed using the Bradford Assay, using Bradford BSA as the standard, and final purity using a 15% SDS-PAGE. The purified recombinant human cardiac troponin I was stored at −20° C.

EXAMPLE 2

Expression and purification of troponin T

Human cardiac troponin T was cloned and expressed as previously described (Hu et al., 1996, Protein Expression and Purification, vol. 7, pp. 289–293, the full disclosure of which is incorporated herein by reference). According to this method, the codons of two consecutive pairs of AGG codons in the human cardiac troponin T cDNA were replaced in order to achieve a high level of expression in E. coli. The replacements were with synonymous codons thus the protein produced from this expression vehicle was not altered (see FIG. 2; SEQ ID NO:6). A 40-fold increased expression was achieved. This E. coli strain has been deposited and has ATCC number.

For purification of recombinant troponin T, the following reagents were used: lysis buffer: (50 mM Tris-HCl, 1 mM EDTA, 20 mM 2-mercaptoethanol, 100 mM sodium chloride, pH 8.0); dialysis buffer 1 (50 mM Tris-HCl, 500 mM potassium chloride, 5 mM 2-mercaptoethanol, 1 mM EDTA, pH 8.0); dialysis buffer II (50 mM Tris-HCl, 5 mM 2-mercaptoethanol, pH 8.0); eluting buffer (50 mM Tris-HCl, 500 mM sodium chloride, 5 mM 2-mercaptoethanol, pH 8); storage buffer (50 mM Tris-HCl, 100 mM sodium chloride, 5 mM 2-mercaptoethanol, pH 7.5).

Purification of recombinant troponin T was accomplished as follows. Recombinant bacterial cells were collected by centrifugation of the cell culture medium. Cells were resuspend in lysis buffer at the ratio of 50 ml lysis buffer per liter equivalent of culture medium. Lysozyme (10 mg/ml) was added at 1 ml lysozyme per liter of culture medium. For antigen preparation, the resulting mixture was then shaken at room temperature for 30 minutes. Triton X-100 (10%) was added at 5 ml per liter of original culture medium, followed by PMSF (0.1M) at 0.5 ml of PMSF per liter of medium. The suspension was incubated at 37° C. for 15 minutes. The vessel containing the suspension was submerged into dry ice/ethanol to rapidly freeze the cell suspension. The frozen suspension was then thawed in a 37° C. water bath. The thawed cell suspension was sonicated using a Vibra Cell™ sonicator at 2° C.–8° C. to shear the DNA. The suspension was centrifuged at 20,000 g for 20 min at 2° C.–8° C. and the pellet was discarded. The supernatant was dialyzed in dialysis buffer I overnight, and if required, the dialysate was centrifuged to remove any particular matter.

The troponin T in the supernatant was precipitated with 30–50% ammonium sulfate by adding the required amount of solid ammonium sulfate slowly and stirring for 30 min. The precipitated protein was dissolved in and dialyzed against dialysis buffer II overnight, and then if required, centrifuged to remove any particulate matter. The sample was loaded onto a previously equilibrated DEAE-Bio-gel column (for example, 2.5×20 cm; 100 ml bed volume for 2 L of equivalent cell culture medium volume). After washing the column with 4 bed volumes of the dialysis buffer II, protein was eluted with a linear gradient of 3.5 bed volumes of 0–800 mM NaCl (dialysis buffer II changed over to eluting buffer). The fractions were checked using 15% SDS-PAGE and the recombinant human cardiac troponin T fractions pooled then dialyzed against storage buffer. The dialysate was then centrifuged at 20,000 g for 20 min and the supernatant filtered through two layers of Miracloth.

In order to remove endotoxin from the protein preparation to produce an antigen, following Triton X-114 phase separation procedures are performed. Triton X-114 (100%) was added at 1 ml per 100 ml of the supernatant and stirred at 4° C. for 30 min. The sample was incubated at 37° C. for 10 min., then centrifuged at 20,000 g for 5 min at 30° C. using 40-ml centrifuge tubes. After removing the upper aqueous phase with care so as not to aspirate the detergent phase, the aqueous phases were combined. The addition and centrifugation steps with Triton X-114 were repeated two more times. The aqueous phase was dialyzed overnight against the storage buffer (100 ml sample per liter of the final buffer).

Final determination of protein concentration was performed using the Bradford Assay, with BSA as the standard, and final purity using a 15% SDS-PAGE. Recombinant human cardiac troponin T was stored at −20° C.

EXAMPLE 3

Expression and purification of troponin C

Human cardiac troponin C cDNA was cloned using the polymerase chain reaction (PCR) using primers designed from the published cardiac troponin C cDNA sequence (GenBank AC: X07897). The cDNA sequence was confirmed by DNA sequencing and cloned into plasmid pET21 (Novagen). E. coli BL21(DE3) cells (Novagen) were transformed with the resulting construct and protein expression analyzed by SDS-PAGE.

For purification, reagents included lysis buffer (50 mM Tris-HCl, 1 mM EDTA, 20 mM 2-mercaptoethanol, 100 mM sodium chloride, pH 8.0); and storage buffer (50 mM Tris-HCl, 200 mM sodium chloride, 1mM CaCl2, pH 7.5).

Purification of recombinant human cardiac troponin C was accomplished as follows. Recombinant bacterial cells were collected by centrifugation of the cell culture. Cells were resuspend in lysis buffer at the ratio of 50 ml lysis buffer per liter equivalent of cell culture medium. Lysozyme (10 mg/ml) was added at 1 ml per liter of culture medium. The resulting mixture was then shaken at room temperature for 30 minutes. Triton X-100 (10%) was added at 5 ml per liter of original medium, followed by PMSF (0.1M) at 0.5 ml per liter of cell culture. The suspension was incubated at 37° C. for 15 minutes. The vessel containing the suspension was submerged into dry ice/ethanol to rapidly freeze the cell suspension. The frozen suspension was then thawed in a 37° C. water bath. The thawed cell suspension was sonicated using a Vibra Cell™ sonicator at 2° C.–8° C. to shear the DNA. The suspension was centrifuged at 20,000 g for 20 min at 2° C.–8° C. and the pellet was discarded. The supernatant was dialyzed in storage buffer overnight, and if required, the dialysate was centrifuged to remove any particular matter.

The supernatant was treated with 70% ammonium sulfate by adding the required amount of solid ammonium sulfate slowly and stirring for 30 min. After centrifugation, the troponin C in the supernatant was dialyzed against storage buffer overnight, then centrifuged if necessary to remove any particulate matter. The sample was concentrated in an Amicon filter to 10 ml per liter equivalent cell culture column, then was loaded on pre-equilibrated Bio-gel P60 size exclusion column. The protein was eluted with storage buffer. Fractions were checked by 15% SDS-PAGE, and the fractions containing recombinant human cardiac troponin C pooled.

In order to remove endotoxin from the protein preparation, following Triton X-114 phase separation procedures are performed. Triton X-114 (100%) was added at 1 ml per 100 ml of eluate, and the mixture was stirred at 4° C. for 30 min. Then incubated at 37° C. for 10 min. The mixture was then centrifuged at 20,000 g for 5 min. Using 40-ml centrifuge tubes, and the upper phase aspirated carefully to avoid taking the detergent phase. Aqueous phases were combined, and the detergent step repeated twice more. The aqueous phase was dialyzed against dialysis buffer overnight.

Protein concentration was determined using the Bradford Assay, with BSA as the standard. The recombinant human cardiac troponin C was lyophilized and stored at −20° C.

EXAMPLE 4

Post-purification folding of three subunits into a troponin C-I-T complex

The following reagents were used: 1.0 mg/ml recombinant human cardiac troponin I, 1.0 mg/ml recombinant human cardiac troponin C, and 1.0 mg/ml recombinant human cardiac troponin T, purified as described in the above examples; 2% sodium dodecyl sulfate; 400 mM $CaCl_2$; 400 mM MgCl2; final buffer (20 mM Tris-HCl, 500 mM NaCl, 60 mM 2-mercaptoethanol, pH 7.5); storage buffer (10 mM Phosphate buffered saline, pH 6.8, 3% normal bovine serum, 4 mM $CaCl_2$, 4 mM $MgCl_2$, protease inhibitors, and 0.05% thimerosal).

The following procedure was employed. Ten µl of 1.0 mg/ml recombinant troponin I and 10 µl of 2% SDS are combined in a microcentrifuge tube. The microcentrifuge tube was placed in a boiling water bath for 5 min., then cooled at room temperature for 5 min. Ten µl of 1.0 mg/ml recombinant troponin C, 10 µl of 1.0 mg/ml recombinant troponin T, 10 µl of 400 mM $CaCl_2$, and 10 µl of 400 mM $MgCl_2$ were added. The mixture was shaken at room temperature for 5 min., then 940 µl of the final buffer was added and the mixture shaken for an additional 25 minutes at room temperature. The above mixture was diluted into the storage buffer at 0.5 ml per 100 ml. The complex was stored at 4° C. or lyophilized.

This protocol can be scaled up proportionally to prepare larger batches of recombinant troponin complex.

EXAMPLE 5

Comparison of recombinant troponin complex stability to that of the tissue-derived complex The stability of the recombinant cardiac troponin complex produced by the above procedures was compared directly to that of a human cardiac troponin complex prepared from human heart tissue in accordance with the protocol described in EP 0 743 522. The lyophilized powder form of the recombinant troponin complex was rehydrated and the stability monitored after reconstitution. Day 0 corresponds to the day of rehydration. After rehydration, the samples were stored at 4° C. and aliquots taken for assay at the indicated times. The initial (time 0) concentrations of each preparation are arbitrary and are not meant for comparison across experiments, but only with regard to stability over time. The data, expressed in ng/ml as measured by the Stratus(R) troponin I assay, are a follows:

TABLE 1

| Calibrators | Storage Conditions | Time Duration (days) | | | | |
|---|---|---|---|---|---|---|
| | | 0 | 2 | 7 | 14 | 28 |
| Recombinant human cardiac troponin complex in accordance with the present invention | 4 C. | 14.9 | 15.12 | 16.0 | 16.5 | 15.0 |
| | lyophilized powder after reconstitution and stored at 4 C. | 10.7 | N/a | 10.3 | 11.1 | 10.4 |
| Cardiac tissue troponin complex prepared according to EP 0 743 522 | 4 C. | 24.4 | 23.4 | 21.5 | 22.6 | 20.0 |
| | lyophilized powder after reconstitution and stored at 4 C. | 22.4 | N/a | 19.4 | 19.5 | 18.5 |

As is apparent from the data presented in Table 1, the recombinant troponin complex prepared by the method of the present invention maintained its detectability by Stratus (R) assay for 28 days at 4° C., whereas the tissue-derived human cardiac troponin complex suffered a 17–18% loss of detectability during 28 days of storage.

EXAMPLE 6

Comparison of troponin concentration determinations among various troponin I assays Two commercial troponin I calibrators as well as the recombinant cardiac troponin complex prepared as described above were evaluated with two commercial troponin I assays and by ELISA. The concentration of recombinant human cardiac troponin I was based on protein mass as measured by Bradford using BSA as the standard. The results are presented in the following table.

TABLE 2

| Troponin source | Stated concentration (ng/ml) | Assay results (ng/ml) | | |
|---|---|---|---|---|
| | | ELISA | Stratus (R) | Access (R) |
| Procedure described in the present invention | 25.00 | 26.98 | 21.65 | 22.45 |
| Stratus (R) troponin I calibrator | 27.2 | 0 | 27.9 | 0 |
| Access (R) troponin I calibrator | 23.34 | n/a | 39.5 | 27.4 |

As is apparent from the data presented in Table 2, each troponin source was detected near its stated concentration by the assay manufactured by that troponin source; however, in both cases the commercially-available troponin I failed to assay consistently across all assays. The troponin complex of the present invention was the only preparation measurable within reasonable limits across the assays.

Similar studies with the individual subunits of the novel complex show their improved stability and utility as standards or calibrators.

EXAMPLE 7

Preparation of a complex of troponin I and troponin C

The following reagents were used: 1.0 mg/ml recombinant human cardiac troponin I and 1.0 mg/ml recombinant human cardiac troponin C prepared and purified as described in the above examples, 10M urea in distilled water, 400 mM $CaCl_2$, and 400 mM $MgCl_2$. The Final Buffer contained 200 mM Tris-HCl, 500 mM NaCl, and 60 mM β-mercaptoethanol, pH 7.5.

The following procedure was employed. Ten μl of 1.0 mg/ml troponin I and 20 μl of 10M urea were combined in a microcentrifuge tube. The tube was shaken gently for 5 minutes at room temperature. Ten μl of 1.0 mg/ml troponin C, 10 μl of 400 mM $CaCl_2$, and 10 μl of 400 mM $MgCl_2$ were then added to the tube, which was then shaken gently for 5 minutes at room temperature, after which 940 μl of Final Buffer was added and the tube was gently shaken at room temperature for 25 minutes. This mixture can be stored at −20° C. or lyophilized.

---

What is claimed is:

1. A recombinant human cardiac troponin I-troponin T-troponin C complex comprising a modified recombinant human cardiac troponin I, recombinant human cardiac troponin T and recombinant human cardiac troponin C, wherein the expression in *E. coli* of said modified recombinant troponin I is increased compared to that of a recombinant troponin I having a native protein sequence and wherein said modified recombinant troponin I consists of the native troponin I protein sequence with an N-terminal extension, said extension consisting of about 5 to about 8 amino acid residues including an N-terminal methionine.

2. The complex of claim 1 wherein the recombinant troponin I has a sequence identified as (SEQ ID NO:5).

3. A purified recombinant human cardiac troponin I-troponin T-troponin C complex comprising a modified recombinant human cardiac troponin I, human cardiac troponin T and human cardiac troponin C, wherein the expression in *E. coli* of said modified recombinant troponin I is increased compared to that of a recombinant troponin I having a native protein sequence and wherein said modified recombinant troponin I consists of the native troponin I protein sequence with an N-terminal extension, said extension consisting of about 5 to about 8 amino acid residues including an N-terminal methionine.

4. The complex of claim 3 in which the recombinant troponin I has a sequence identified as (SEQ ID NO:5).

5. A modified recombinant human cardiac troponin I wherein the expression in *E. coli* of said modified recombinant troponin I is increased compared to that of a recombinant troponin I having a native protein sequence and wherein said modified recombinant troponin I consists of the native troponin I protein sequence with an N-terminal extension, said extension consisting of about 5 to about 8 amino acid residues including an N-terminal methionine.

6. The modified recombinant human cardiac troponin I of claim 5 having the amino acid sequence set forth in (SEQ ID NO:5).

7. A recombinant human cardiac troponin I-troponin C complex comprising a modified recombinant human cardiac troponin I, and recombinant human cardiac troponin C, wherein the expression in *E. coli* of said modified recombinant troponin I is increased compared to that of a recombinant troponin I having a native protein sequence and wherein said modified recombinant troponin I consists of the native troponin I protein sequence with an N-terminal extension, said extension consisting of about 5 to about 8 amino acid residues including an N-terminal methionine.

8. The recombinant human cardiac troponin complex of claim 7 wherein the recombinant troponin I has a sequence identified as (SEQ ID NO:5).

9. A purified recombinant human cardiac troponin I-troponin C complex comprising a modified recombinant human cardiac troponin I and human cardiac troponin C, wherein the expression in *E. coli* of said modified recombinant troponin I is increased compared to that of a recombinant troponin I having a native protein sequence and wherein said modified recombinant troponin I consists of the native troponin I protein sequence with an N-terminal extension, said extension consisting of about 5 to about 8 amino acid residues including an N-terminal methionine.

10. The complex of claim 9 which the recombinant troponin I has a sequence identified as (SEQ ID NO:5).

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 651 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:1:

| | | | | | |
|---|---|---|---|---|---|
| ATGGCTAGCA | TGGGATCTAT | GGCAGACGGT | TCCAGCGATG | CGGCTAGGGA | ACCTCGCCCT | 60 |
| GCACCAGCCC | CAATCAGACG | CCGCTCCTCC | AACTACCGCG | CTTATGCCAC | GGAGCCGCAC | 120 |
| GCCAAGAAAA | AATCTAAGAT | CTCCGCCTCG | AGAAAATTGC | AGCTGAAGAC | TCTGCTGCTG | 180 |
| CAGATTGCAA | AGCAAGAGCT | GGAGCGAGAG | GCGGAGGAGC | GGCGCGGAGA | GAAGGGGCGC | 240 |
| GCTCTGAGCA | CCCGCTGCCA | GCCGCTGGAG | TTGGCCGGGC | TGGGCTTCGC | GGAGCTGCAG | 300 |
| GACTTGTGCC | GACAGCTCCA | CGCCCGTGTG | GACAAGGTGG | ATGAAGAGAG | ATACGACATA | 360 |
| GAGGCAAAAG | TCACCAAGAA | CATCACGGAG | ATTGCAGATC | TGACTCAGAA | GATCTTTGAC | 420 |
| CTTCGAGGCA | AGTTTAAGCG | GCCCACCCTG | CGGAGAGTGA | GGATCTCTGC | AGATGCCATG | 480 |
| ATGCAGGCGC | TGCTGGGGGC | CCGGGCTAAG | GAGTCCCTGG | ACCTGCGGGC | CCACCTCAAG | 540 |
| CAGGTGAAGA | AGGAGGACAC | CGAGAAGGAA | AACCGGGAGG | TGGGAGACTG | GCGCAAGAAC | 600 |
| ATCGATGCAC | TGAGTGGAAT | GGAGGGCCGC | AAGAAAAAGT | TTGAGAGCTG | A | 651 |

( 2 ) INFORMATION FOR SEQ ID NO:2:

( i ) SEQUENCE CHARACTERISTICS:
        ( A ) LENGTH: 867 base pairs (B) TYPE: nucleic acid
(C) STRANDEDNESS: double
(D) TOPOLOGY: linear (ii) MOLECULE TYPE: cDNA (iii) HYPOTHETICAL: NO (xi) SEQUENCE DESCRIPTION: SEQ ID NO:2:

| | | | | | | |
|---|---|---|---|---|---|---|
| ATGTCTGACA | TAGAAGAGGT | GGTGGAAGAG | TACGAGGAGG | AGGAGCAGGA | AGAAGCAGCT | 60 |
| GTTGAAGAGC | AGGAGGAGGC | AGCGGAAGAG | GATGCTGAAG | CAGAGGCTGA | GACCGAGGAG | 120 |
| ACCAGGGCAG | AAGAAGATGA | AGAAGAAGAG | GAAGCAAAGG | AGGCTGAAGA | TGGCCCAATG | 180 |
| GAGGAGTCCA | AACCAAAGCC | CAGGTCGTTC | ATGCCCAACT | TGGTGCCTCC | CAAGATCCCC | 240 |
| GATGGAGAGA | GAGTGGACTT | TGATGACATC | CACCGGAAGC | GCATGGAGAA | GGACCTGAAT | 300 |
| GAGTTGCAGG | CGCTGATTGA | GGCTCACTTT | GAGAACAGGA | AGAAAGAGGA | GGAGGAGCTC | 360 |
| GTTTCTCTCA | AAGACAGGAT | CGAGAGACGT | CGGGCAGAGC | GGGCCGAGCA | GCAGCGCATC | 420 |
| CGGAATGAGC | GGGAGAAGGA | GCGGCAGAAC | CGCCTGGCTG | AAGAGAGGGC | TCGACGAGAG | 480 |
| GAGGAGGAGA | ACCGTCGTAA | GGCTGAGGAT | GAGGCCCGGA | AGAAGAAGGC | TTTGTCCAAC | 540 |
| ATGATGCATT | TTGGGGGTTA | CATCCAGAAG | CAGGCCCAGA | CAGAGCGGAA | AAGTGGGAAG | 600 |
| AGGCAGACTG | AGCGGGAAAA | GAAGAAGAAG | ATTCTGGCTG | AGCGTCGTAA | GGTGCTGGCC | 660 |
| ATTGACCACC | TGAATGAAGA | TCAGCTGAGG | GAGAAGGCCA | AGGAGCTGTG | GCAGAGCATC | 720 |
| TATAACTTGG | AGGCAGAGAA | GTTCGACCTG | CAGGAGAAGT | TCAAGCAGCA | GAAATATGAG | 780 |
| ATCAATGTTC | TCCGAAACAG | GATCAACGAT | AACCAGAAAG | TCTCCAAGAC | CCGCGGGAAG | 840 |
| GCTAAAGTCA | CCGGGCGCTG | GAAATAG | | | | 867 |

(2) INFORMATION FOR SEQ ID NO:3:

(i) SEQUENCE CHARACTERISTICS:
(A) LENGTH: 651 base pairs
(B) TYPE: nucleic acid
(C) STRANDEDNESS: double
(D) TOPOLOGY: linear (ii) MOLECULE TYPE: cDNA
(A) DESCRIPTION: native form (iii) HYPOTHETICAL: NO (xi) SEQUENCE DESCRIPTION: SEQ ID NO:3:

| | | | | | | |
|---|---|---|---|---|---|---|
| ATGGCTAGCA | TGGGATCTAT | GGCGGATGGG | AGCAGCGATG | CGGCTAGGGA | ACCTCGCCCT | 60 |
| GCACCAGCCC | CAATCAGACG | CCGCTCCTCC | AACTACCGCG | CTTATGCCAC | GGAGCCGCAC | 120 |
| GCCAAGAAAA | AATCTAAGAT | CTCCGCCTCG | AGAAAATTGC | AGCTGAAGAC | TCTGCTGCTG | 180 |
| CAGATTGCAA | AGCAAGAGCT | GGAGCGAGAG | GCGGAGGAGC | GGCGCGGAGA | GAAGGGGCGC | 240 |
| GCTCTGAGCA | CCCGCTGCCA | GCCGCTGGAG | TTGGCCGGGC | TGGGCTTCGC | GGAGCTGCAG | 300 |
| GACTTGTGCC | GACAGCTCCA | CGCCCGTGTG | GACAAGGTGG | ATGAAGAGAG | ATACGACATA | 360 |
| GAGGCAAAAG | TCACCAAGAA | CATCACGGAG | ATTGCAGATC | TGACTCAGAA | GATCTTTGAC | 420 |
| CTTCGAGGCA | AGTTTAAGCG | GCCCACCCTG | CGGAGAGTGA | GGATCTCTGC | AGATGCCATG | 480 |
| ATGCAGGCGC | TGCTGGGGGC | CCGGGCTAAG | GAGTCCCTGG | ACCTGCGGGC | CCACCTCAAG | 540 |
| CAGGTGAAGA | AGGAGGACAC | CGAGAAGGAA | AACCGGGAGG | TGGGAGACTG | GCGCAAGAAC | 600 |
| ATCGATGCAC | TGAGTGGAAT | GGAGGGCCGC | AAGAAAAAGT | TGAGAGCTG | A | 651 |

(2) INFORMATION FOR SEQ ID NO:4:

( i ) SEQUENCE CHARACTERISTICS:
- ( A ) LENGTH: 867 base pairs
- ( B ) TYPE: nucleic acid
- ( C ) STRANDEDNESS: double
- ( D ) TOPOLOGY: linear ( i i ) MOLECULE TYPE: cDNA
- ( A ) DESCRIPTION: native form ( i i i ) HYPOTHETICAL: NO ( x i ) SEQUENCE DESCRIPTION: SEQ ID NO:4:

```
ATGTCTGACA TAGAAGAGGT GGTGGAAGAG TACGAGGAGG AGGAGCAGGA AGAAGCAGCT      60
GTTGAAGAGC AGGAGGAGGC AGCGGAAGAG GATGCTGAAG CAGAGGCTGA GACCGAGGAG     120
ACCAGGGCAG AAGAAGATGA AGAAGAAGAG GAAGCAAAGG AGGCTGAAGA TGGCCCAATG     180
GAGGAGTCCA AACCAAAGCC CAGGTCGTTC ATGCCCAACT TGGTGCCTCC CAAGATCCCC     240
GATGGAGAGA GAGTGGACTT TGATGACATC CACCGGAAGC GCATGGAGAA GGACCTGAAT     300
GAGTTGCAGG CGCTGATTGA GGCTCACTTT GAGAACAGGA AGAAAGAGGA GGAGGAGCTC     360
GTTTCTCTCA AAGACAGGAT CGAGAGACGT CGGGCAGAGC GGGCCGAGCA GCAGCGCATC     420
CGGAATGAGC GGGAGAAGGA GCGGCAGAAC CGCCTGGCTG AAGAGAGGGC TCGACGAGAG     480
GAGGAGGAGA ACAGGAGGAA GGCTGAGGAT GAGGCCCGGA AGAAGAAGGC TTTGTCCAAC     540
ATGATGCATT TTGGGGGTTA CATCCAGAAG CAGGCCCAGA CAGAGCGGAA AAGTGGGAAG     600
AGGCAGACTG AGCGGGAAAA GAAGAAGAAG ATTCTGGCTG AGAGGAGGAA GGTGCTGGCC     660
ATTGACCACC TGAATGAAGA TCAGCTGAGG GAGAAGGCCA AGGAGCTGTG GCAGAGCATC     720
TATAACTTGG AGGCAGAGAA GTTCGACCTG CAGGAGAAGT TCAAGCAGCA GAAATATGAG     780
ATCAATGTTC TCCGAAACAG GATCAACGAT AACCAGAAAG TCTCCAAGAC CCGCGGGAAG     840
GCTAAAGTCA CCGGGCGCTG GAAATAG                                         867
```

( 2 ) INFORMATION FOR SEQ ID NO:5:

( i ) SEQUENCE CHARACTERISTICS:
- ( A ) LENGTH: 216 amino acids
- ( B ) TYPE: amino acid
- ( C ) STRANDEDNESS: single
- ( D ) TOPOLOGY: linear ( i i ) MOLECULE TYPE: protein ( i i i ) HYPOTHETICAL: NO ( x i ) SEQUENCE DESCRIPTION: SEQ ID NO:5:

```
Met Ala Ser Met Gly Ser Met Ala Asp Gly Ser Ser Asp Ala Ala Arg
 1               5                  10                  15
Glu Pro Arg Pro Ala Pro Ala Pro Ile Arg Arg Arg Ser Ser Asn Tyr
                20                  25                  30
Arg Ala Tyr Ala Thr Glu Pro His Ala Lys Lys Lys Ser Lys Ile Ser
                35                  40                  45
Ala Ser Arg Lys Leu Gln Leu Lys Thr Leu Leu Leu Gln Ile Ala Lys
            50                  55                  60
Gln Glu Leu Glu Arg Glu Ala Glu Glu Arg Arg Gly Glu Lys Gly Arg
 65                 70                  75                  80
Ala Leu Ser Thr Arg Cys Gln Pro Leu Glu Leu Ala Gly Leu Gly Phe
                85                  90                  95
Ala Glu Leu Gln Asp Leu Cys Arg Gln Leu His Ala Arg Val Asp Lys
               100                 105                 110
```

```
Val  Asp  Glu  Glu  Arg  Tyr  Asp  Ile  Glu  Ala  Lys  Val  Thr  Lys  Asn  Ile
          115                      120                     125

Thr  Glu  Ile  Ala  Asp  Leu  Thr  Gln  Lys  Ile  Phe  Asp  Leu  Arg  Gly  Lys
          130                      135                     140

Phe  Lys  Arg  Pro  Thr  Leu  Arg  Arg  Val  Arg  Ile  Ser  Ala  Asp  Ala  Met
145                           150                     155                     160

Met  Gln  Ala  Leu  Leu  Gly  Ala  Arg  Ala  Lys  Glu  Ser  Leu  Asp  Leu  Arg
                         165                     170                     175

Ala  His  Leu  Lys  Gln  Val  Lys  Lys  Glu  Asp  Thr  Glu  Lys  Glu  Asn  Arg
               180                      185                     190

Glu  Val  Gly  Asp  Trp  Arg  Lys  Asn  Ile  Asp  Ala  Leu  Ser  Gly  Met  Glu
          195                      200                     205

Gly  Arg  Lys  Lys  Lys  Phe  Glu  Ser
          210                      215
```

(2) INFORMATION FOR SEQ ID NO:6:

(i) SEQUENCE CHARACTERISTICS:
      (A) LENGTH: 288 amino acids
      (B) TYPE: amino acid
      (C) STRANDEDNESS: single
      (D) TOPOLOGY: linear (ii) MOLECULE TYPE: protein (iii) HYPOTHETICAL: NO (xi) SEQUENCE DESCRIPTION: SEQ ID NO:6:

```
Met  Ser  Asp  Ile  Glu  Val  Val  Glu  Glu  Tyr  Glu  Glu  Glu  Glu  Glu  Gln
1                        5                   10                      15

Glu  Glu  Ala  Ala  Val  Glu  Glu  Gln  Glu  Glu  Ala  Ala  Glu  Glu  Asp  Ala
               20                      25                      30

Glu  Ala  Glu  Ala  Glu  Thr  Glu  Glu  Thr  Arg  Ala  Glu  Glu  Asp  Glu  Glu
               35                      40                      45

Glu  Glu  Glu  Ala  Lys  Glu  Ala  Glu  Asp  Gly  Pro  Met  Glu  Glu  Ser  Lys
          50                       55                      60

Pro  Lys  Pro  Arg  Ser  Phe  Met  Pro  Asn  Leu  Val  Pro  Pro  Lys  Ile  Pro
65                           70                      75                      80

Asp  Gly  Glu  Arg  Val  Asp  Phe  Asp  Asp  Ile  His  Arg  Lys  Arg  Met  Glu
                    85                       90                      95

Lys  Asp  Leu  Asn  Glu  Leu  Gln  Ala  Leu  Ile  Glu  Ala  His  Phe  Glu  Asn
               100                     105                     110

Arg  Lys  Lys  Glu  Glu  Glu  Glu  Leu  Val  Ser  Leu  Lys  Asp  Arg  Ile  Glu
          115                     120                     125

Arg  Arg  Arg  Ala  Glu  Arg  Ala  Glu  Gln  Gln  Arg  Ile  Arg  Asn  Glu  Arg
          130                     135                     140

Glu  Lys  Glu  Arg  Gln  Asn  Arg  Leu  Ala  Glu  Glu  Arg  Ala  Arg  Arg  Glu
145                           150                     155                     160

Glu  Glu  Glu  Asn  Arg  Arg  Lys  Ala  Glu  Asp  Glu  Ala  Arg  Lys  Lys  Lys
                    165                     170                     175

Ala  Leu  Ser  Asn  Met  Met  His  Phe  Gly  Gly  Tyr  Ile  Gln  Lys  Gln  Ala
               180                     185                     190

Gln  Thr  Glu  Arg  Lys  Ser  Gly  Lys  Arg  Gln  Thr  Glu  Arg  Glu  Lys  Lys
          195                     200                     205

Lys  Lys  Ile  Leu  Ala  Glu  Arg  Arg  Lys  Val  Leu  Ala  Ile  Asp  His  Leu
          210                     215                     220

Asn  Glu  Asp  Gln  Leu  Arg  Glu  Lys  Ala  Lys  Glu  Leu  Trp  Gln  Ser  Ile
225                           230                     235                     240
```

-continued

| Tyr | Asn | Leu | Glu | Ala | Glu | Lys | Phe | Asp | Leu | Gln | Glu | Lys | Phe | Lys | Gln |
|     |     |     |     | 245 |     |     |     |     | 250 |     |     |     |     | 255 |     |

| Gln | Lys | Tyr | Glu | Ile | Asn | Val | Leu | Arg | Asn | Arg | Ile | Asn | Asp | Asn | Gln |
|     |     |     | 260 |     |     |     |     | 265 |     |     |     |     | 270 |     |     |

| Lys | Val | Ser | Lys | Thr | Arg | Gly | Lys | Ala | Lys | Val | Thr | Gly | Arg | Trp | Lys |
|     |     | 275 |     |     |     |     | 280 |     |     |     |     | 285 |     |     |     |